US006671638B2

(12) United States Patent
Kitazumi et al.

(10) Patent No.: US 6,671,638 B2
(45) Date of Patent: Dec. 30, 2003

(54) OSCILLATION MEASURING METHOD AND FREQUENCY MEASURING APPARATUS

(75) Inventors: Hitoshi Kitazumi, Shizuoka (JP); Tetsuro Maruyama, Shizuoka (JP); Junji Watanabe, Shizuoka (JP); Yoshimitsu Nishimura, Chiba (JP); Hiroshi Kodera, Tokyo (JP); Masao Sumi, Tokyo (JP)

(73) Assignee: Suzuki Motor Corporation, Shizuoka (JP)

( * ) Notice: Subject to any disclaimer, the term of this patent is extended or adjusted under 35 U.S.C. 154(b) by 250 days.

(21) Appl. No.: 09/781,163

(22) Filed: Feb. 13, 2001

(65) Prior Publication Data

US 2001/0016799 A1 Aug. 23, 2001

(30) Foreign Application Priority Data

Feb. 15, 2000 (JP) ........................................ 2000-036568

(51) Int. Cl.[7] .............................................. G01R 23/00
(52) U.S. Cl. ........................................ 702/75; 356/5.09
(58) Field of Search ..................... 702/75, 76, 124, 702/126, 189, FOR 103, FOR 104, FOR 107, FOR 108, FOR 134; 356/5.09, 28, 28.5, 139, 477, 488, 499; 250/206, 277.11, 339.13

(56) References Cited

U.S. PATENT DOCUMENTS

| 3,811,774 A | * | 5/1974 | Honeycutt et al. .......... 356/5.09 |
| 3,825,341 A | * | 7/1974 | Goto ........................... 356/28 |
| 3,891,321 A | * | 6/1975 | Hock .......................... 356/488 |
| 3,958,881 A | | 5/1976 | Keene et al. .................. 356/28 |
| 4,311,383 A | * | 1/1982 | Ohtsubo ...................... 356/28.5 |
| 5,166,942 A | * | 11/1992 | Cardimona et al. ............ 372/21 |
| 5,179,418 A | * | 1/1993 | Takamiya et al. ........... 356/28.5 |
| 5,216,478 A | * | 6/1993 | Kadowaki et al. .......... 356/28.5 |
| 5,587,785 A | * | 12/1996 | Kato et al. .................. 356/28.5 |
| 6,437,855 B1 | * | 8/2002 | Wilson et al. .............. 356/28.5 |
| 2002/0176087 A1 | * | 11/2002 | Numai ....................... 356/461 |

FOREIGN PATENT DOCUMENTS

DE          4006690        9/1991

OTHER PUBLICATIONS

"Laser Doppler Velocimeter Using the Self–Mixing Effect of a Semiconductor Laser Diode" by Shinohara et al., Applied Optics, May, 1986, vol. 25(9), pp. 1417–1419.

"Approximate theory and Characteristics of Laser Doppler Velocimeter Using Self–Mixing Effect of Semiconductor Laser Diodes" by Shinohara et al., Electronics and Communications in Japan, part 2, 1989, vol. 72, pp. 444–452.

"Automatic Measurement of Velocity and Length of Moving Plate Using Self–Mixing Laser Diode" by Shibata et al., IEEE Trans. IM, Dec., 1999, vol. 48(6), pp. 1062–1067.

"Self–Mixing Effect of the Semiconductor Laser Doppler Method for Blood Flow Measurement" by Mito et al., Medical and Biological Engineering and Computing, May, 1993, vol. 31, pp. 308–310.

* cited by examiner

Primary Examiner—Marc S. Hoff
Assistant Examiner—Mohamed Charioui
(74) Attorney, Agent, or Firm—Greenblum & Bernstein, P.L.C.

(57) ABSTRACT

The present invention provides an oscillation measuring method comprising: a laser beam emission step S1 for emitting a laser beam to an object to be measured; a return beam reception step S2 for receiving a return beam reflected by the object and having an object Doppler frequency according to a velocity of the object; a self-mixing step S3 for mixing the return beam having the Doppler frequency with another beam emitted upon reception of the return beam and generating a self-frequency according to a resonator change during a time from the emission to the reception of the return beam, so as to generate a beat wave containing the object Doppler frequency superposed with the self-frequency; and an oscillation information output step S4 for outputting the beat wave or information obtained from signal processing of the beat wave as the object oscillation information. This enables to measure a fine oscillation of an object to be measured.

9 Claims, 13 Drawing Sheets

CHARACTERISTIC OF MAXIMUM DOPPLER BEAT
FREQUENCY fdmax AGAINST THE TIME LAPSE t ( $f_{sp}$ = 1kHz. $f_m$ =1k+0.9mHz. $f_{bmax}$ =184.5kHz. $f_{dmax}$ =134.5kHz)

FINE FREQUENCY DIFFERENCE fw
CALCULATED AGAINST SAMPLING INTERVAL

OSCILLATION MEASURING METHOD AND FREQUENCY MEASURING APPARATUS

BACKGROUND OF THE INVENTION

1. Field of the Invention

The present invention relates to an oscillation measurement method and a frequency measurement apparatus and in particular, to an oscillation measurement method and a frequency measurement apparatus for measuring an oscillation state of an object by using a self-mixing type laser Doppler oscillation meter.

The present invention can be applied to an inspection and calibration apparatus for an oscillation generating apparatus and to apparatus of an abnormal oscillation detection in a power apparatus operating for a long period of time. As the inspection/calibration apparatus, the present invention can be applied for inspection of a frequency of, for example, a crystal oscillator and an ultrasonic oscillator and for calibration of a function generator. Moreover, as the abnormal oscillation detection apparatus, the present invention can be applied to a detection apparatus for a frequency deviation caused by undesirable resonance in a semiconductor manufacturing equipment which utilizing a high frequency oscillation as well as a defect in a tool such as a drill.

The invention can also be applied for purpose of oscillation analysis. More specifically, analysis of engine oscillation, analysis of vehicle body oscillation, analysis of noise in a vehicle, analysis of muffler oscillation, and the like. The invention can also be applied to various production fields. The invention can also be applied for detection of oscillation of a plant using a motor, leak analysis of a water pipe and a gas pipe for maintenance. Furthermore, the invention can be applied to determine sugar content in a large-size fruit such as a watermelon through a hitting sound. Here, the "object" to be measured has a wide range from crystal oscillators to watermelons.

2. Description of the Related Art

Conventionally, as means for measuring a frequency of a vibrating object in non-contact way, there is a method for obtaining a frequency by using a laser displacement meter utilizing the trigonometrical survey.

However, in the aforementioned conventional example, it is impossible to detect a displacement in a short period of time because of the sampling time of the displacement meter and has a problem that an error is caused in the measured oscillation cycle because of the sampling time. This becomes especially remarkable when the object oscillation becomes greater to reduce the difference between the oscillation cycle and the sampling time. That is, a great error is caused unless the sampling cycle is more than twice the maximum oscillation cycle (sampling theorem). Moreover, since the trigonometric survey is used, there is a need of using a large sensor head whose position and direction should be adjusted so that a reflected beam will not be cut off. Accordingly, this cannot be used for measurement in a small space.

SUMMARY OF THE INVENTION

It is therefore an object of the present invention to provide an oscillation measurement method and a frequency measurement apparatus capable of measuring a small oscillation of an object with a high accuracy.

The oscillation measuring method according to the present invention comprises: a laser beam emission step for emitting a laser beam to an object to be measured; a return beam reception step for receiving a return beam reflected by the object and having an object Doppler frequency according to a velocity of the object; a self-mixing step for mixing the return beam having the Doppler frequency with beam emitted itself upon reception of the return beam and generating a self-frequency according to a resonator change during a time from the emission to the reception of the return beam, so as to generate a beat wave containing the object Doppler frequency superposed with the self-frequency; and an oscillation information output step for outputting the beat wave or information obtained from signal processing of the beat wave as the object oscillation information.

The oscillation measuring method according to the present invention measures an oscillation utilizing self-mixing type laser Doppler effect. A return beam having a Doppler frequency according to a velocity change of an object to be measured is self-mixed with an emitted beam generating a self-frequency of the resonator itself. The self-frequency is generated, for example, by a method for driving with a drive current of a sinusoidal waveform having a frequency in the proximity to the self-frequency and a method for physically oscillating the laser block having the resonator. When the resonator is driven by a drive current of a sinusoidal waveform, the oscillated beam has a wavelength changing according to the drive current value, causing a difference between the emitted beam and the return beam. This difference generates a beat wave of the self-frequency in the resonator. When the laser block having the resonator is physically oscillated, a Doppler frequency is generated by the resonator velocity and the velocity of the object to be measured. The Doppler frequency of the self-frequency by the resonator velocity is superposed by the Doppler frequency of the object to be measured. The self-frequency can be considered to be an imaginary velocity of the resonator. In other words, two Doppler frequencies based on two velocity values are mixed. Here, a phrase "having a Doppler frequency" means that a returned beam has a frequency shifted by the Doppler effect and has the shifted component as the Doppler frequency.

When the self-frequency change is in the proximity to the Doppler frequency change, a beat wave is generated according to a difference between the two frequencies. This beat wave has an envelope having a longer cycle as compared to the cycle of the Doppler frequency. Since the frequency of the envelope is a difference between the two frequencies, for example, in a preferred embodiment, it is possible to use this envelope frequency to obtain a difference between a frequency of the object to be measured and a frequency of an imaginary velocity of the resonator. Since the envelope frequency is lower than the Doppler frequency of the object to be measured, the accuracy in obtaining the envelope frequency value is higher than the accuracy in obtaining the Doppler frequency. Accordingly, according to the present invention, it is possible to improve the effective figures of the detectable miunute frequency difference without increasing the accuracy of the A/D converter or the like.

In the laser emission step, a laser beam is emitted to the object to be measured. The laser beam is scattered and reflected by the surface of the object to change its frequency according to the velocity of the object. In the return beam reception step, this return beam is received. In the self-mixing step this return beam is self-mixed in the resonator, with an emitted beam (oscillated beam) emitted upon reception of the return beam. The emitted beam emitted upon reception of the return beam generates a self-frequency according to a resonated change during a period from the laser beam emission to the laser beam reception. Accordingly, in the present invention, a newly emitted beam generating a self-frequency is self-mixed with the return beam having the Doppler frequency of the object to be measured. The oscillation information output step outputs as the oscillation information of the object to be measured a beat wave generated by the mixture of the object Doppler frequency and the self-frequency or information of the beat wave subjected to a signal processing.

This beat wave is useful for detecting a change of the oscillation state of the object to be measured. Especially when the self-frequency is in the proximity to the object oscillation frequency, it is possible to obtain a beat wave characterized in the envelope waveform. From this envelope frequency, it is possible to calculate a fine frequency difference between the modulation-frequency and the object frequency.

Moreover, when the envelope value change is below a predetermined value, it is possible to determine that the self-frequency is matched with the object frequency in valid digits. Accordingly, it is possible to calculate a frequency of the object by successively changing the self-frequency to detect an envelope value change, i.e., by synchronizing the self-frequency with the object frequency.

Moreover, the frequency measuring apparatus according to the present invention comprises: a laser resonator for oscillating a laser beam and self-mixing the laser beam reflected by an object to be measured and returning as a return beam with a laser beam emitted upon reception of the return beam; a laser drive block for driving the laser resonator with a laser drive current of a sinusoidal wave; a laser block for emitting a laser beam oscillated with a wavelength according to the drive current in the laser resonator to the object to be measured and outputting a beat wave obtained from self-mixture in the resonator, of a return beam from the object with an emitted beam oscillated with a wavelength according to a drive current in the laser resonator upon reception of the return beam; and a signal processing block for performing signal processing of the beat wave output from the laser block and outputting a processed result as an oscillation information, wherein the signal processing block includes a fine frequency difference calculation function for calculating an oscillation frequency of the object according to a frequency change of the beat wave.

In this frequency measuring apparatus, the laser is driven by the laser drive with a laser drive current of a sinusoidal wave. Then, in the resonator, the wavelength of the emitted beam is changed according to the sinusoidal wave. When wavelength of the emitted beam in the resonator is changed, a beat frequency is generated between the emitted beam and the return beam corresponding to turn-around of flight time. When the laser drive current is linearly increased, for example, the beat frequency is constant if the object to be measured is in a still state. In this invention, since the laser drive current is input as a sinusoidal waveform, the beat frequency according to the oscillated wavelength change is changed with a cycle of the laser drive current waveform. This beat frequency change is the self-frequency. Accordingly, in the frequency measuring apparatus according to the present invention, the wavelength change of the emitted beam (oscillated beam) is assumed to be an imaginary velocity of the resonator, and the corresponding beat frequency is used as the self-frequency. Moreover, the Doppler frequency is changed according to a velocity change of the object to be measured. When the object is oscillating, the velocity is 0 at the oscillation return position where the velocity direction is reversed. If a sinusoidal wave oscillation is assumed, then the object velocity is changed with a sinusoidal waveform. In this case, the Doppler frequency is also changed with a sinusoidal wave.

When the laser drive is performed with a sinusoidal wave and the object is moving, the return beam has an object Doppler frequency. Then, in the beat wave generated by the self-mixing in the resonator, the self-frequency is superposed by the object frequency (Doppler frequency). The cycle change of this beat wave is based on a fine frequency difference between the self-frequency and the object frequency. Accordingly, by observing the cycle change of this beat wave, it is possible to measure a difference between the object to be measured and the self-frequency as well as a frequency of the object and an oscillation cycle change of the object.

BRIEF DESCRIPTION OF THE DRAWINGS

FIG. 3 shows waveforms for explaining the operation principle of the present invention.

FIG. 4 shows waveforms for explaining the operation principle of the present invention.

FIG. 7 is a block diagram showing a detailed configuration of a laser drive system in FIG. 6.

FIG. 10 shows waveforms as a measurement result of the Doppler beat frequency along a time lapse.

FIG. 12 shows an example of an envelope-approximated waveform used in an example of reducing a measurement time by approximation of an envelope.

FIG. 13 shows an example of waveform as a calculation result by the approximation.

DESCRIPTION OF THE PREFERRED EMBODIMENTS

Figure 1:
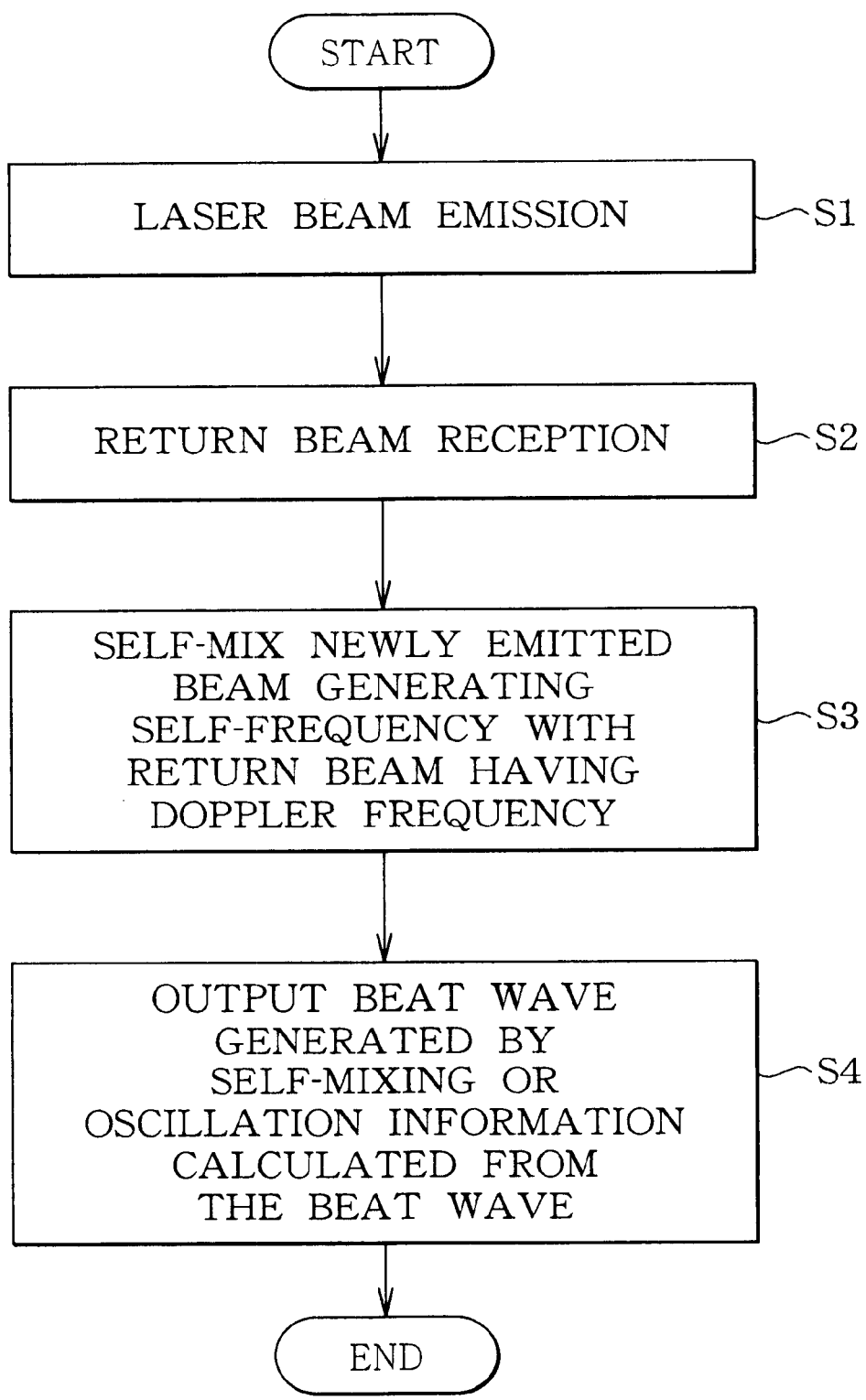
FIG. 1 is a flowchart showing a configuration of a first embodiment of the present invention.

Description will now be directed to an embodiment of the present invention with reference to the attached drawings. FIG. 1 is a flowchart showing a configuration example of the oscillation measurement method according to the present invention. As shown in FIG. 1, the oscillation measurement method according to this embodiment includes: a laser beam emitting step S1 for emitting a laser beam to an object to be measured; a beam reception step S2 for receiving a return beam reflected by the object and having an object Doppler frequency according to a velocity of the object; a self-mixing step S3 for self-mixing a new beam with the return beam, i.e., a beam oscillated and emitted upon reception of the return beam at the return beam reception step S2 and generating a self-frequency according to a change of a resonator from the laser beam emission moment to the return beam, with the return beam having the Doppler frequency; and an oscillation information output step S4 for outputting a beat wave generated in the self-mixing step S3 having the object Doppler frequency superposed with the self-frequency or information after the beat wave is subjected to a signal processing.

Figure 2:
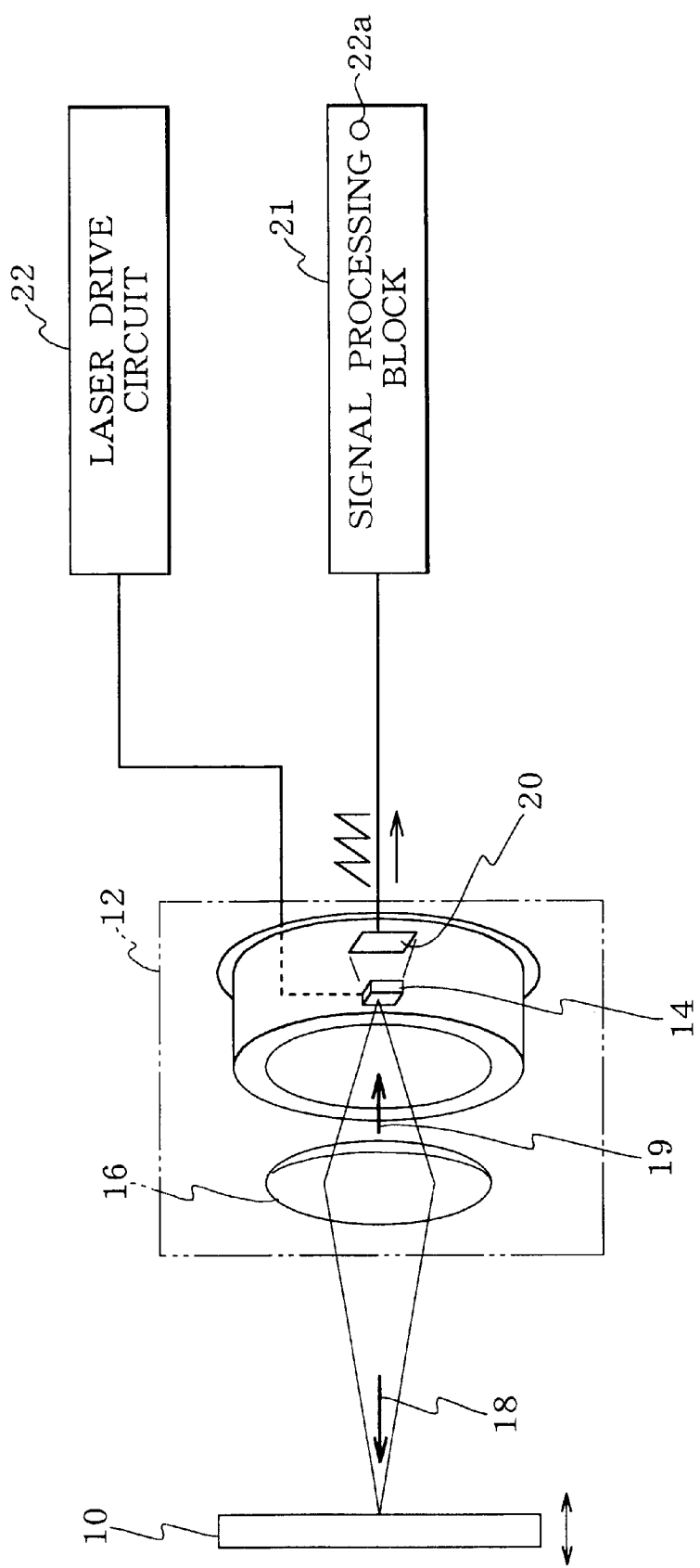
FIG. 2 explains a configuration of hardware resources in the first embodiment.

FIG. 2 shows a configuration of an oscillation measuring apparatus (or a frequency measuring apparatus) that can preferably be applied for carrying out the oscillation measuring method. For an object 10, a velocity change at the position where the laser beam is reflected, a cycle of the velocity change, and a frequency are measured. The oscillation measuring apparatus includes a laser block 12, a lens 16 for focusing a beam emitted from the laser block 12 and a return beam scattered by the object, and a signal processing block 21 supplied with a beat wave generated by self-mixing of the return beam received at the laser block 12 and the beam emitted.

The laser block 12 includes a laser diode 14 having a laser resonator 14, and a photo diode 20 for photoelectric conversion of the beat wave output from the laser resonator 14. The signal processing block 21 has hardware resources such as a personal computer, a microcomputer, and an analog circuit for processing the beat wave.

Referring back to FIG. 1, in the laser beam emission step S1, a laser resonator driven by a predetermined laser drive current oscillates and an oscillated laser beam is emitted to an object to be measured. This beam is scattered and reflected at the surface of the object 10 and a part of the reflected beam returns to the laser resonator 14 (S2). The return beam is self-mixed with a new beam emitted and when the emitted beam and the return beam differ in the frequency, a beat wave is generated according to the frequency difference.

In this invention, during the self-mixing of the emitted beam and the return beam, two types of frequency changes are superposed. When the two frequencies are similar to each other, a frequency beat is generated. If this beat is periodically changed, the two types of frequencies are not identical though similar to each other. By measuring a cycle of the beat caused by the two types of frequencies, it is possible to obtain a difference between the two frequencies. Such a frequency difference obtained from the beat cycle can improve the measurement accuracy (valid numerals). Accordingly, if the A/D conversion sampling rate is assumed to be identical, then a measurement based on the beat cycle can further improve the measurement accuracy than directly measuring a frequency. On the other hand, the calculation based on the beat cycle requires more time. For example, when the quantization accuracy is relatively high as compared to the sampling rate, it is possible to approximately obtain a high accuracy without waiting one beat cycle.

For this, in the present embodiment, two types of frequencies are mixed by self-mixing between the return beam and the emitted beam within the laser resonator 14. One is the Doppler frequency according to the velocity of the object, which appears as a change of frequency of the return beam. The other is the self-frequency of the resonator. When the resonator generates the self-frequency, the resonator itself can be vibrated physically. Then, according to the resonator velocity, two types of Doppler frequencies are superposed.

To generate a self-frequency while the resonator is fixed, in this embodiment, a wavelength difference is generated between an emitted beam and a return beam. The emitted beam has a first frequency (wavelength) which is scattered and reflected as a return beam by the object at a still state. Then, the return beam has the first frequency. Before this return beam reaches the resonator, the frequency of an emitted beam is changed to a second frequency. The return beam having the first frequency is self-mixed with the return beam having the second frequency, causing a beat wave according to a difference between the first frequency and the second frequency. In general, the oscillation frequency in the laser resonator changes according to the laser drive current value within a range not causing a mode hop. For this, by changing the laser drive current, it is possible to generate a frequency difference between the emitted beam and the return beam.

When the laser drive current is linearly increased, the oscillated frequency is increased linearly and the beat wave frequency remains constant. That is, when the laser drive current is linearly increased and the object to be measured is in a still state, the beat wave has a constant frequency. On the other hand, the Doppler frequency of the object to be measured is changed according to the velocity of the object. When the object is vibrating, the velocity is maximum at the center of the oscillation and zero at the return point where the velocity direction is reversed. Accordingly, the Doppler frequency is periodically changed along the time axis according to the object velocity change.

Since every waveform can be expressed as a combinations of sinusoidal waves, when the object to be measured in simple harmonic oscillation, the Doppler frequency is increased and decreased with the oscillation cycle. Accordingly, the waveform obtained by FV conversion of the beat wave is a sinusoidal wave. This Doppler frequency change waveform is the first waveform while the resonator self-frequency change waveform is the second wave. By combining this first wave and the second wave, it is possible to obtain an envelope indicate a group frequency similar as a group velocity. Since this envelope shows the beat cycle, it is possible to accurately calculate a difference between the Doppler frequency change cycle and the self-frequency change wave cycle.

When the laser drive current to the laser resonator 14 is changed, the wavelength is changed. The wavelength change differentiated by time is a wavelength change velocity (oscillation frequency change velocity). When the laser drive current is increased linearly, the wavelength change velocity is constant and accordingly, the beat frequency is also constant. Since this embodiment requires a change waveform of the self-frequency, the laser drive current is made to be a sinusoidal waveform. Then, the wavelength change velocity is expressed as a sinusoidal waveform. In this case, the beat frequency is also expressed as a sinusoidal wave having an identical cycle. The beat frequency change assuming this laser drive current as a sinusoidal wave is a self-frequency change waveform.

Accordingly, when the laser resonator is driven with a sinusoidal wave having a cycle in proximity with the oscillation cycle of the object to be measured, a change of the self-frequency is generated assuming the wavelength change velocity as an imaginary velocity. By analyzing the beat wave generated by superpose between the Doppler frequency change and the self-frequency change, it is possible to obtain a difference between the self-frequency change cycle and the Doppler frequency change cycle.

Thus, in step S3, by self-mixing of a newly emitted beam generating a self-frequency with the return beam having the Doppler frequency, a beat wave is generated according to a difference between the self-frequency change and the Doppler frequency change.

Subsequently, in step S4, the beat wave generated by the self-mixing or the oscillation information calculated from the beat wave is output. As an example of signal processing for the beat wave, step S4 may include an envelope extraction step for extracting an envelope of a beat wave frequency change waveform and an oscillation difference calculation step for calculating an oscillation difference between the object Doppler frequency and the self-frequency according to the frequency of the envelope extracted in the envelope extraction step.

The envelope of the beat wave frequency change waveform is the waveform showing the beat caused by the difference between the self-frequency cycle and the Doppler frequency cycle. From this envelope cycle, it is possible to calculate a difference between the self-frequency cycle and the Doppler frequency cycle.

In the configuration shown in FIG. 2, the signal processing block 21 includes a fine frequency difference calculation function 22a for realizing step S4 shown in FIG. 1. The fine frequency difference calculation function 22a calculates the oscillation frequency of the object according to the beat wave frequency change.

As has been described above, according to the present embodiment, it is possible to measure an oscillation of an object with a high accuracy by using a compact and cheap configuration consisting of, for example, a semiconductor laser, an A/D converter, an FV conversion element, and a microcomputer capable of performing digital signal processing. This configuration enables to preferably measure a fine oscillation having a small amplitude and a small oscillation cycle.

Moreover, it is possible to generate a change of the self-frequency by oscillating the resonator itself. This can preferably be applied to a case for detecting a frequency change in one of two objects which are to oscillate with the same frequency. In this case, a laser block 12 is arranged on a second object which oscillates with the same frequency as the first object. The signal processing block 21 has a fine oscillation difference calculation function for calculating a frequency difference between the frequency of the first object and the frequency of the second object. This enables to detect an oscillation frequency difference between two oscillating objects with a high accuracy.

EXAMPLE

In this example, instead of measuring a frequency of an oscillating object alone, the frequency of the oscillating object is compared to a reference having a known frequency in proximity of the oscillation, so as to measure a fine frequency difference. Even if a small error is involved in the measurement of the frequency of the oscillating object, because the fine frequency difference changes periodically as a large change along the time, the error has a very small affect. When the oscillating object oscillates with a great frequency, the reference is also set to a high frequency so as to provide a great difference between the fine frequency difference change cycle and the sampling time, thereby enabling to perform a highly-accurate measurement.

Sinusoidal Wave Modulation Drive

The reference utilizes a characteristic that when a semiconductor laser drive current is changed, an oscillated wavelength is proportionally changed. In the self-mixing type laser Doppler oscillation meter, the semiconductor laser has a sinusoidal wave modulation frequency which is used as a reference to detect a fine frequency difference between the reference and an oscillating object. This enables to perform a measurement with an accuracy determined by the frequency stability of a sinusoidal wave generation circuit.

Figure 3A:
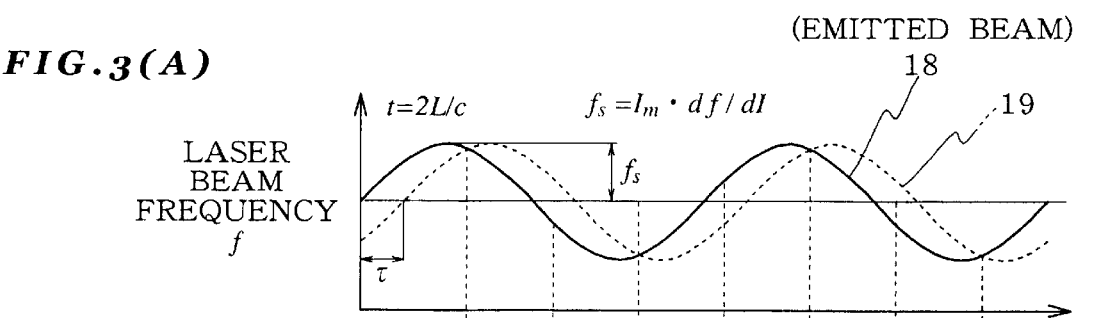
FIG. 3(A) shows a change in the laser beat frequency.
Figure 3B:
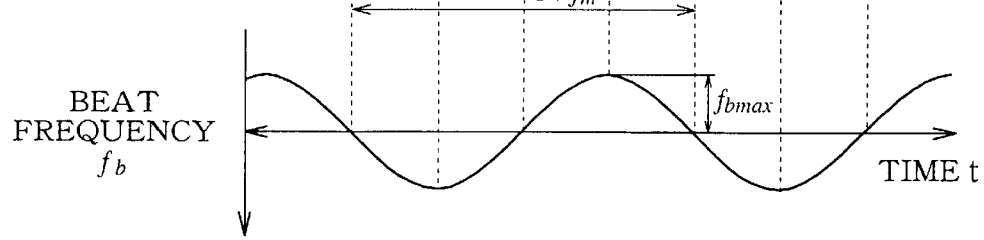
FIG. 3(B) shows a beat frequency change thereof.

When the laser resonator 14 is driven by a sinusoidal wave having a frequency $f_m$ and the object to be measured in a still state, the laser beam emitted from the laser block 12 and the laser beam reflected by the object have different frequencies, which are mixed in the resonator to generate a beat frequency $f_b$. Referring to FIG. 3(A), the emitted laser beam 18 has a frequency identical to the sinusoidal wave modulation frequency of the laser resonator. If it is assumed that the emitted beam 18 takes time τ to travel ravels to and is scattered-reflected by the object and return as the return beam 19 to the resonator, the return beam 18 has a waveform with a phase changed by τ. As shown in FIG. 3(B), when the emitted beam 18 and the return beam 19 are self-mixed, the beat frequency $f_b$ is periodically changed.

If it is assumed that $I_m$ is the modulation current of the laser resonator 14, L is the distance between the semiconductor laser and the object to be measured, c is the light velocity and df/di is the frequency modulation efficiency of the semiconductor laser, then the beat frequency $f_b$ can be expressed by Equation (1) below.

Figure 3C:
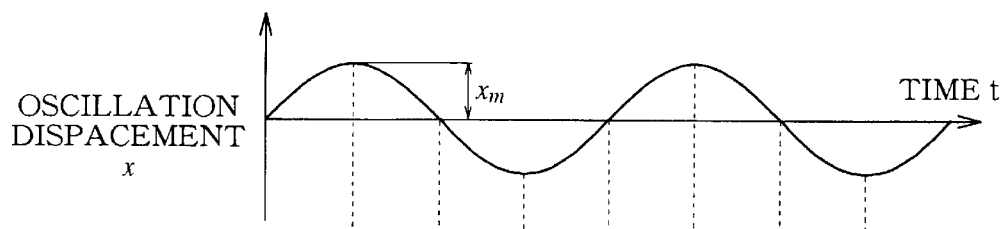
FIG. 3(C) shows an oscillation displacement.
Figure 3D:
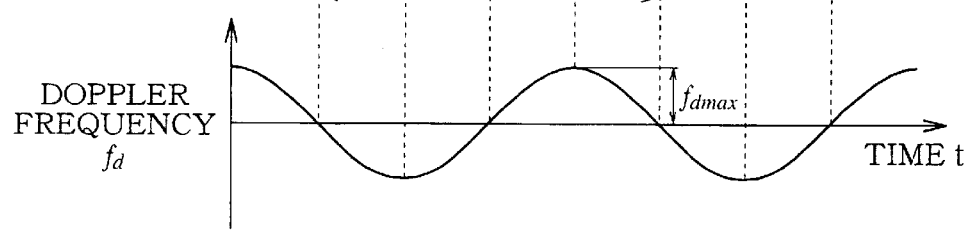
FIG. 3(D) shows a Doppler frequency change thereof.

Moreover, when the laser resonator 14 is driven by a constant current and the object is oscillating with a frequency $f_t$ as shown in FIG. 3(C), the frequency of the reflected beam is changed by the Doppler effect due to the movement of the object, the emitted beam and the return beam are mixed to generate a Doppler frequency $f_d$ as shown in FIG. 3(D). If it is assumed that the laser resonator 14 has an oscillation wavelength λ and the object has an oscillation amplitude $x_m$, then the Doppler frequency $f_d$ can be expressed by Equation (2) below. When the laser resonator 14 is subjected to a sinusoidal wave modulation with a frequency $f_m$ and the object to be measured is oscillating with a frequency $f_t$, a Doppler beat frequency $f_{db}$ corresponding to a sum of them is generated (see Equation (3)).

$$f_b = 4\pi I_m f_m \frac{L}{c} \frac{df}{di} \cos 2\pi f_m t \quad (1)$$
$$= f_{bmax} \cos 2\pi f_m t$$

$$f_d = \frac{4\pi}{\lambda} x_m f_t \cos 2\pi f_t t \quad (2)$$
$$= f_{dmax} \cos 2\pi f_t t$$

-continued $$f_{db} = f_b + f_d \quad (3)$$
$$= f_{bmax}\cos 2\pi f_m t + f_{dmax}\cos 2\pi f_t t$$

$$\left|\frac{1}{T_1} - \frac{1}{T_2}\right| = \frac{1}{T_3} \quad (4)$$

Figure 4A:
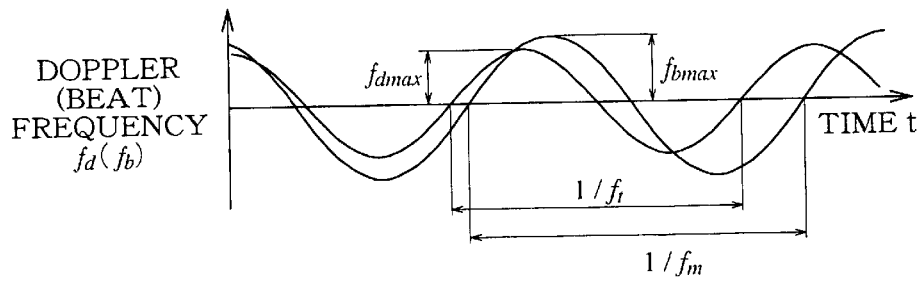
FIG. 4(A) shows a Doppler frequency change and a beat frequency change.
Figure 4B:
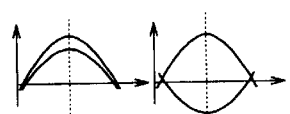
FIG. 4(B) shows a state when they are superposed.

Here, when $f_m$ and $f_t$ are close as shown in FIG. 4(A), in $f_{db}$, a change corresponding to the fine frequency difference $f_a$ with respect to $f_t$ appears as a waveform envelope as shown in FIG. 4(B). By measuring the frequency of this envelope $f_{dbenv}$, it is possible to obtain the fine frequency difference $f_a$.

Figure 4C:
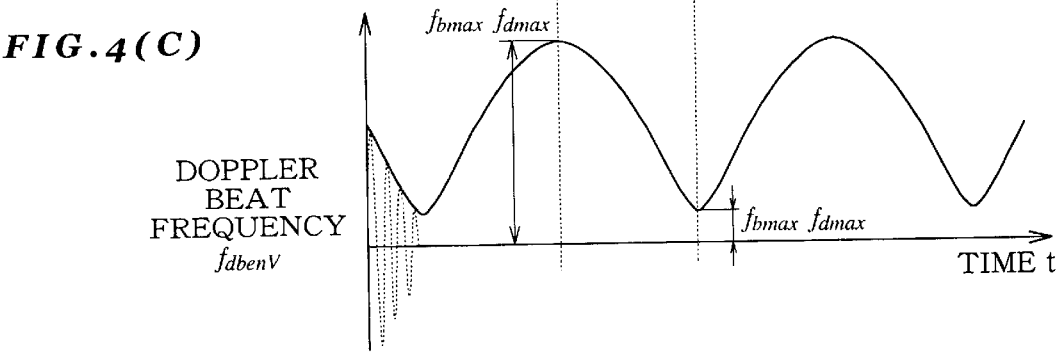
FIG. 4(C) shows an example of the envelope of the Doppler beam frequency change.
Figure 4D:
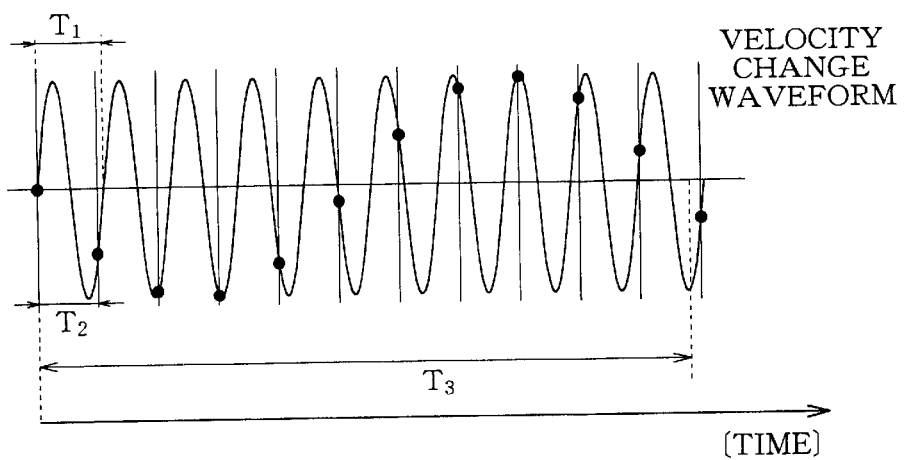
FIG. 4(D) explains the effect of the beat.

As shown in FIG. 4(D), when a wave of cycle $T_1$ is observed by a sampling cycle $T_2$, a beat as a transition of the solid circles in the figure can be observed. When this beat has a cycle $T_3$, the relationship shown in the aforementioned Equation (4) can be obtained.

When the wave of cycle $T_2$ is superposed on the wave of cycle $T_1$, a waveform having an envelope as shown in FIG. 4(C) is obtained. As a wave velocity V is obtained from a frequency multiplied by a wavelength, the two waves shown in FIG. 4(A) can be assumed to be an object velocity change waveform and a resonator imaginary velocity (for example, oscillation frequency change velocity) change waveform. Accordingly, the envelope shown in FIG. 4(C) shows a relative velocity change of the object velocity and the resonator imaginary velocity. Accordingly, a change from a minimum relative velocity difference to a maximum relative velocity difference is repeated. The cycle of this envelope (two beats) can be handled in the same way as the beat shown in FIG. 4(D). Accordingly, from the envelope frequency and the self-frequency waveform frequency, it is possible to calculate the frequency of the object.

The envelope waveform changes according to a difference ($f_{bmax}-f_{dmax}$) between the amplitude ($f_{dmax}$) of the Doppler frequency change waveform and the amplitude ($f_{bmax}$) of the self-frequency change waveform. The Doppler frequency change waveform amplitude ($f_{dmax}$) is a difference between the maximum frequency and the frequency when no Doppler frequency is present while the self-frequency change waveform amplitude is, for example, a difference the maximum self-frequency when the oscillation frequency change ratio is at maximum and the reference frequency.

Figure 5:
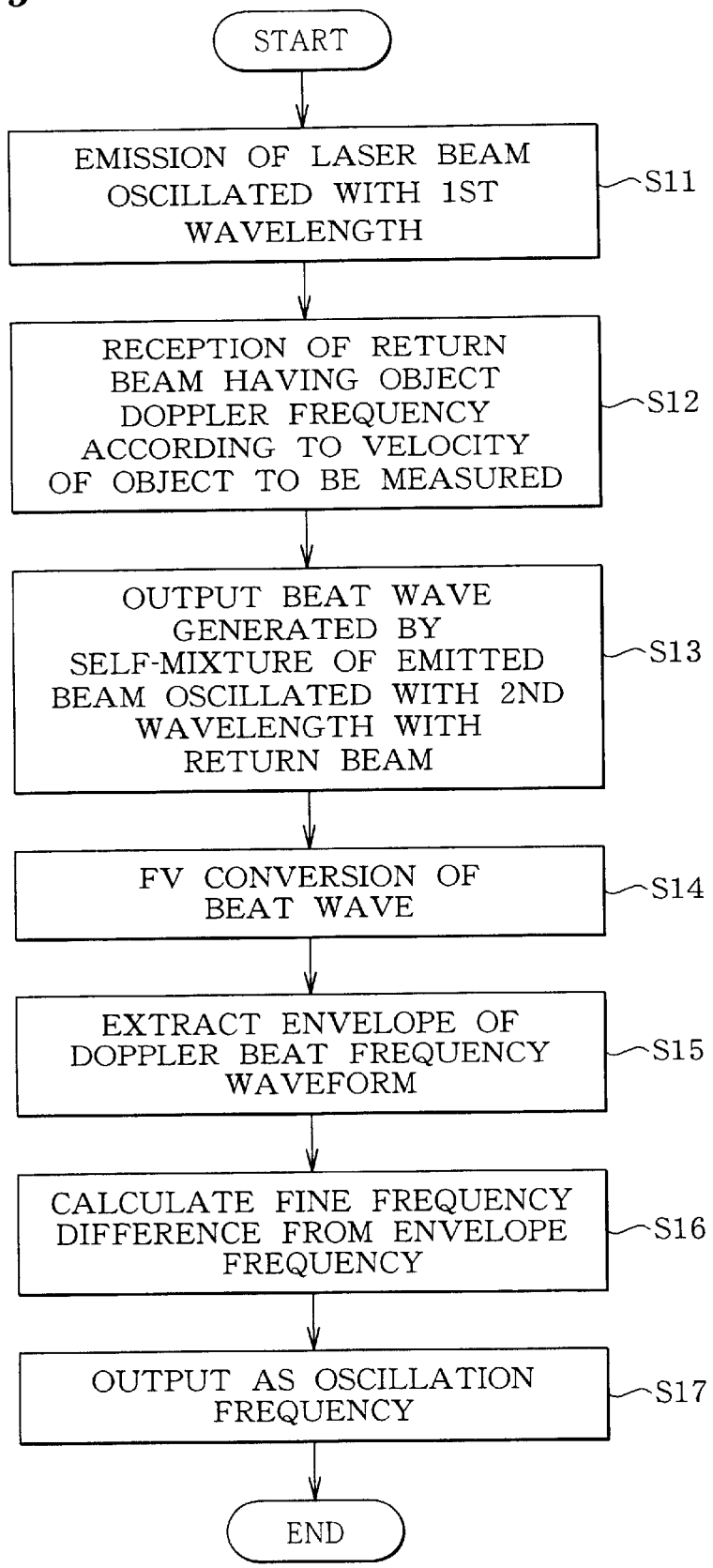
FIG. 5 is a flowchart showing an operation example of the embodiment of the present invention.

FIG. 5 is a flowchart showing an operation example of this example. The laser resonator is assumed to be driven by a drive current which has been subjected to a sinusoidal wave modulation. Firstly, a laser beam is emitted with a first wavelength as the oscillation wavelength according to the value of this drive current (step S11). Next, a return beam having an object Doppler frequency based on the velocity of the object to be measured is received (step S12). Next, the emitted beam having the second wavelength according to the drive current is mixed with a return beam whose wavelength has been changed for time τ required going to and returning from the object, and the resultant beat wave is output (step S13). Next, this beat wave frequency is converted to a voltage value (step S14). Thus, it is possible to obtain a frequency change (or a velocity change if multiplied by a wavelength) waveform. An envelope of this frequency change waveform is extracted (step S15). This envelope has a waveform, for example, as shown in FIG. 4(C).

After extraction of the envelope, a fine frequency difference is calculated from the envelope frequency (step S16). This fine oscillation difference or the frequency of the object to be measured is output as an oscillation information (step S17).

Figure 6:
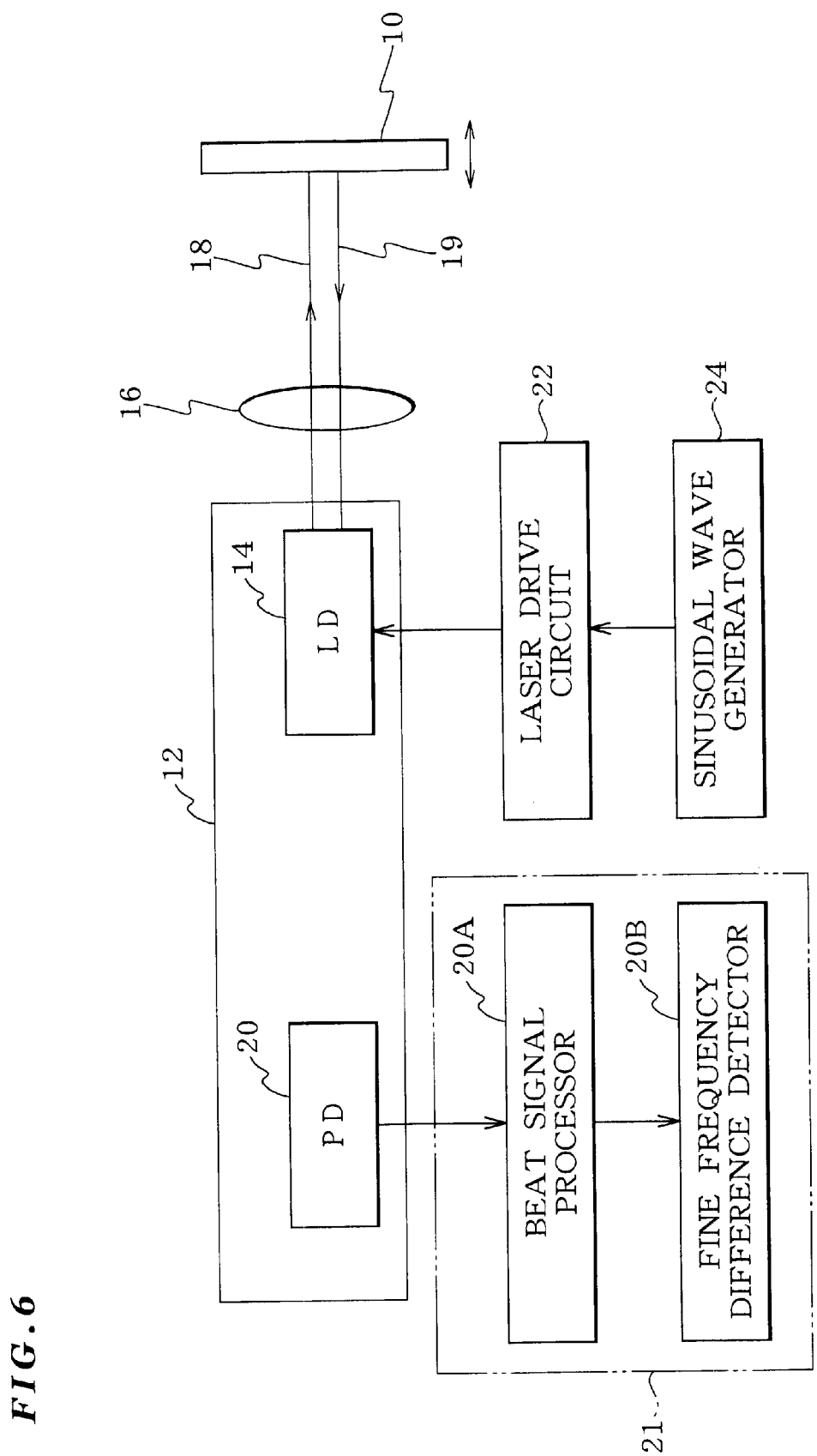
FIG. 6 is a block diagram showing a configuration example of an embodiment of the present invention.

Next, explanation will be given on a detailed configuration of the frequency measuring apparatus with reference to the attached drawings. FIG. 6 is a block diagram showing a configuration example for measuring a fine oscillation. As shown in FIG. 6, the frequency measuring apparatus includes a semiconductor laser block 12 for oscillating a light beam to a surface of an oscillating object oscillating with a constant frequency, a lens 16 for converging this laser beam, a signal processing block 21 for processing the beat wave output from the semiconductor laser block 12, a laser drive circuit 22 for driving the semiconductor laser block 12, and a sinusoidal wave generator 24 for generating a sinusoidal wave used in the laser drive circuit 22. The optical system includes only the lens for converging the laser beam to the object to be measured without requiring expensive optical components, thereby enabling to realize a small-size low-cost apparatus.

The semiconductor laser block 12 includes a laser diode (LD) 14 having a resonator for oscillating a laser beam and self-mixing the emitted laser beam with a return beam, and a photo diode (PD) 20 for detecting a radiating beam from the back surface of the laser diode 14.

The signal processing block 21 includes a beat signal processor 20A for amplifying the beat wave output from the PD 20 and a fine frequency difference detector 20B for calculating a fine frequency difference based on the beat wave.

Figure 7A:
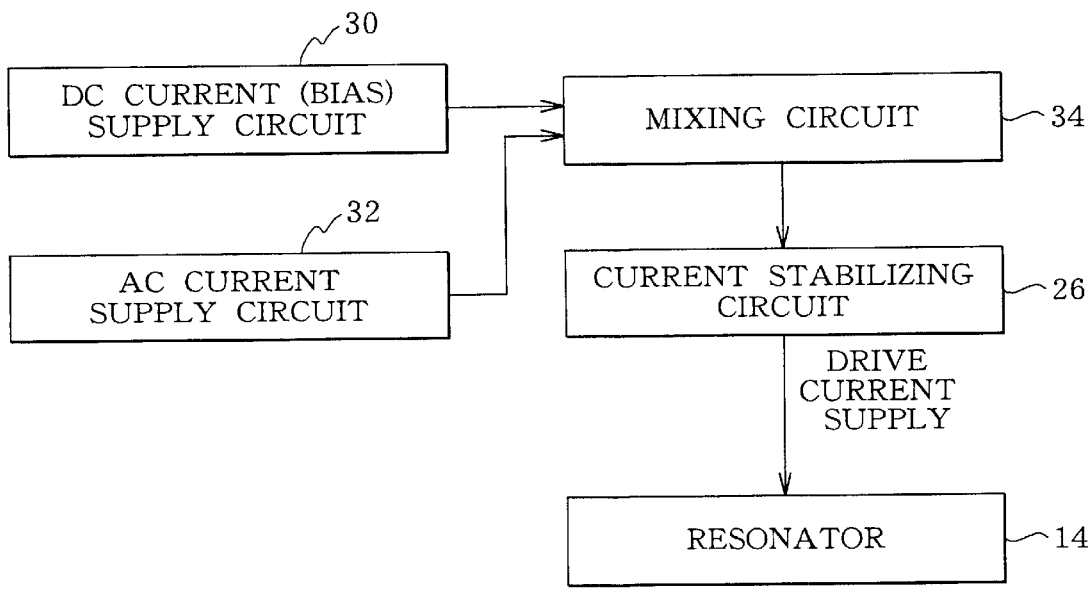
FIG. 7(A) shows an example of generating a sinusoidal wave by AC current.

FIG. 7 is a block diagram showing a configuration example of the laser drive circuit and the sinusoidal wave generator. In the example of FIG. 7(A), a DC current component and an AC current component are supplied to the laser. In this case, the sinusoidal wave generator shown in FIG. 6 is an AC current supply circuit. In this example, the laser drive circuit 22 includes a DC current (bias) supply circuit 30, a mixing circuit 34 for mixing the AC current supplied from the AC current supply circuit and the DC current, and a current stabilizing circuit 26 for stabilizing the current output from this mixing circuit 34.

Figure 7B:
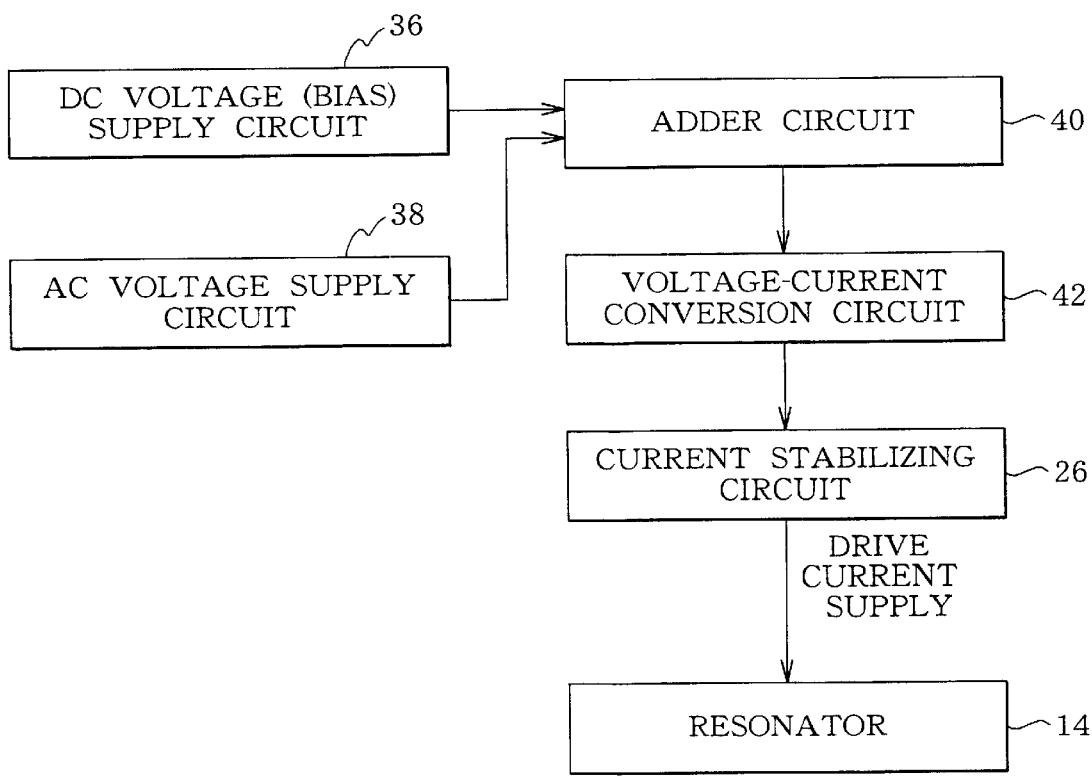
FIG. 7(B) shows an example using voltage.

In FIG. 7(B), a DC voltage and an AC voltage are added to each other and then converted into a current for supply to the laser. In this case, the sinusoidal wave generator 24 is an AC voltage supply circuit 38. In the example of FIG. 7(B), the laser drive circuit 22 includes a DC voltage (bias) supply circuit 36, an adder circuit 40 for adding this bias to the AC voltage, a voltage-current conversion circuit 42 for current value, and a current stabilizing circuit 26 for stabilizing the current change output from the voltage-current conversion circuit 42.

The sinusoidal wave generator 24 generating an AC component of the drive current has a variable frequency. The cycle of the drive current AC component is set to a value in the proximity to the oscillation cycle of the object to be measured. The measurement accuracy in this example depends on the frequency accuracy of the laser drive current. Accordingly, it is preferable to use a sinusoidal wave generator apparatus having a high accuracy.

Figure 8:
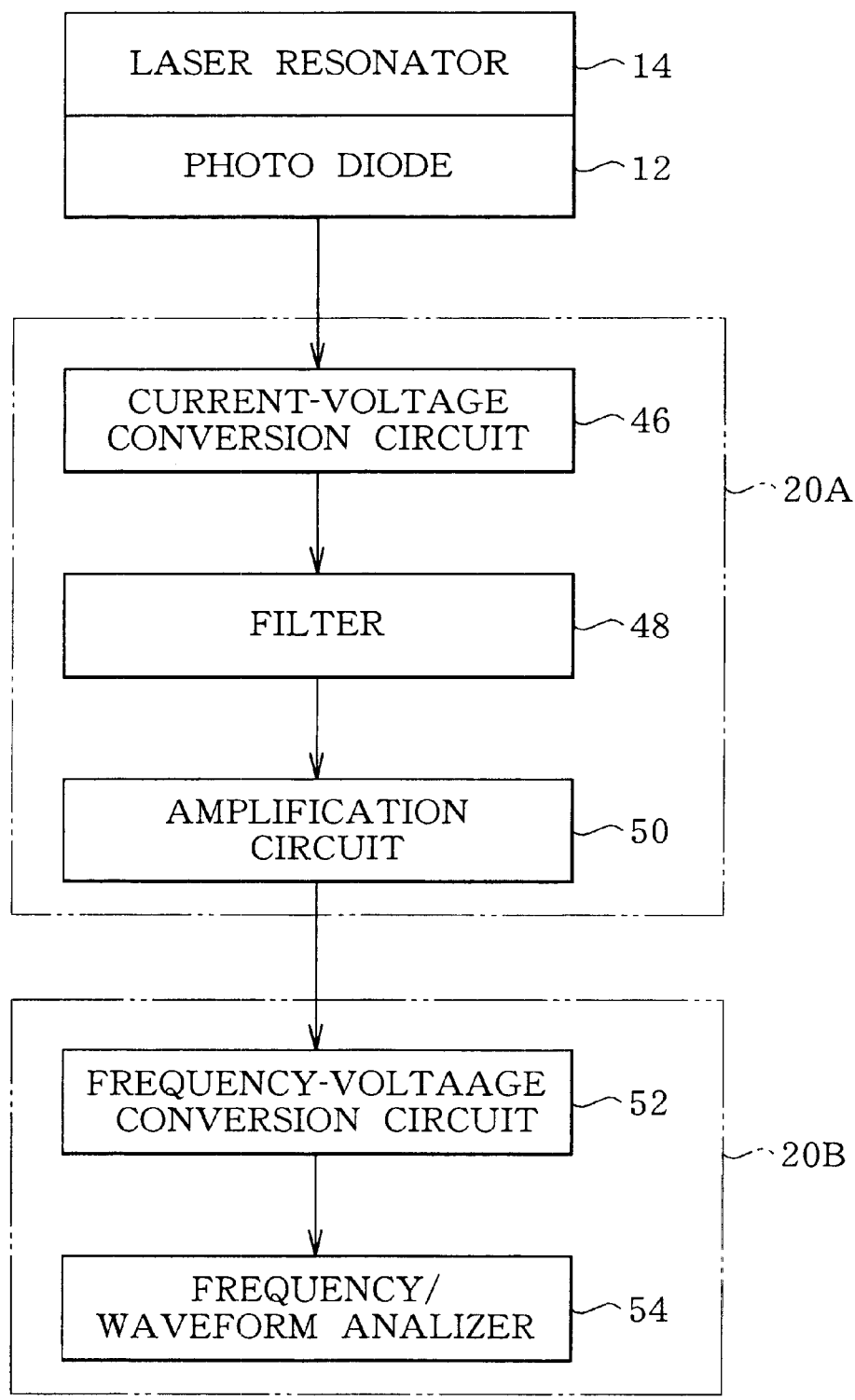
FIG. 8 is a block diagram showing a detailed configuration of the signal processing system shown in FIG. 6.

FIG. 8 shows a configuration of the signal processing system. The beat signal processor 20A includes a current-voltage conversion circuit 46 for converting a current value change of the beat waveform output from the photo diode 12 into a voltage change value, a filter 48 for extracting only a signal generated by the oscillation from the voltage waveform supplied from the current-voltage conversion circuit 46, and an amplification circuit 50 for amplifying the beat wave filtered by this filter 48.

As shown in FIG. 8, the fine frequency detector 20B includes a frequency-voltage conversion circuit (FV conversion element) 52 for converting the beat frequency of the beat wave into a voltage value, and a frequency/waveform analyzer 54 for analyzing the waveform of this frequency change waveform. The frequency/waveform analyzer 54 preferably includes a peak hold block for holding a peak of the voltage value converted by the FV conversion element and outputting the peak value as an envelope waveform of the beat wave. Moreover, this peak hold processing can be performed in a digital manner.

Figure 9:
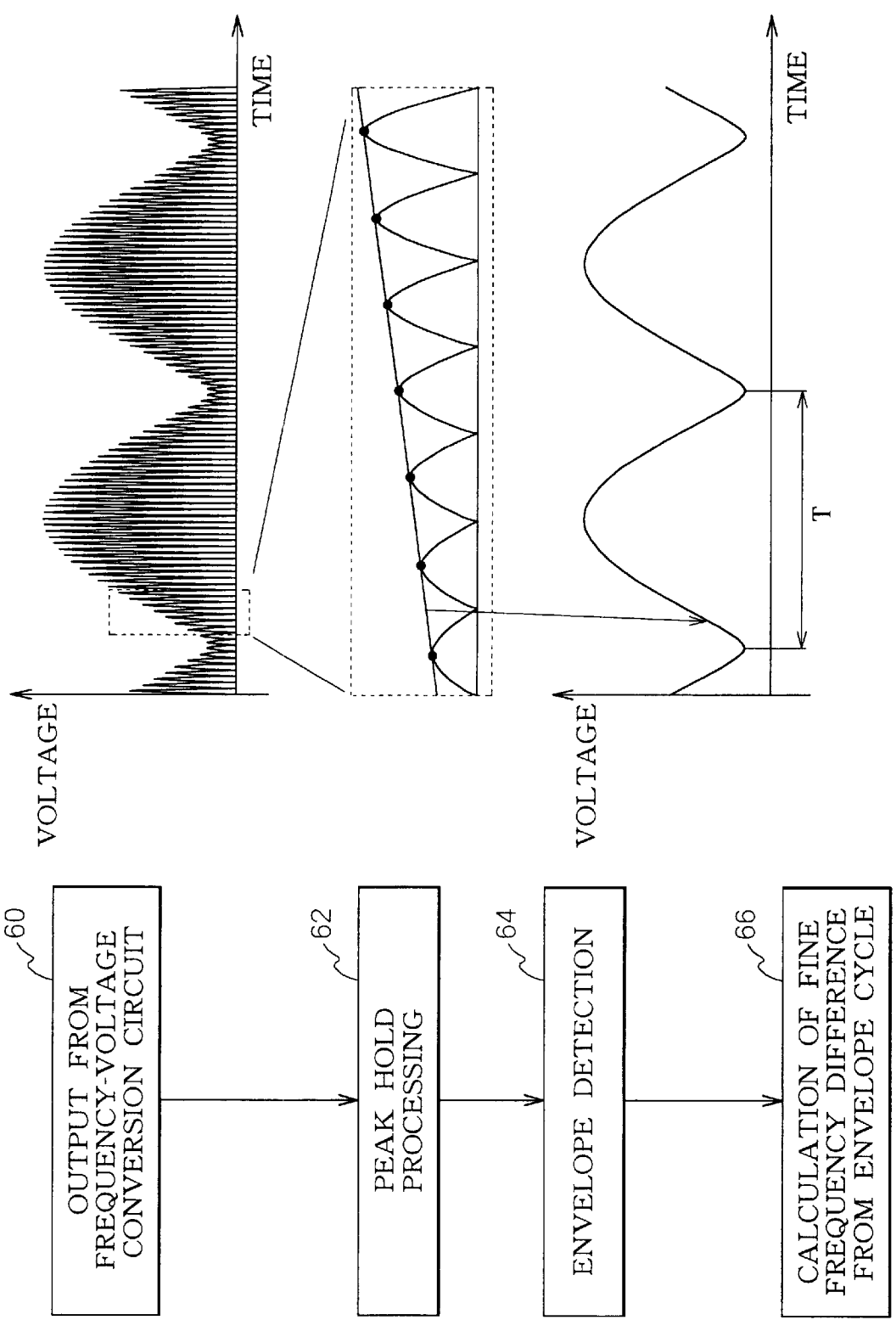
FIG. 9 shows an operation example and a waveform example of the signal processing system shown in FIG. 8.

FIG. 9 explains a processing example by the frequency/waveform analyzer 54. Firstly, an output 60 from the FV conversion circuit 52 has an envelope as shown in FIG. 4(C). The frequency/waveform analyzer 54 performs a peak hold processing 62 to detect the envelope (64). From this envelope cycle T, a fine frequency difference is calculated. That is, in the relationship with the configuration shown in FIG. 2, the fine frequency difference calculation function 22a calculates the frequency difference according to the cycle of the envelope waveform output from the peak hold block.

In the example shown in FIG. 9, the signal output from the frequency-voltage conversion circuit 60 is a waveform having a sinusoidal wave height fluctuating periodically, and this fluctuation cycle is the cycle of the fine frequency difference. This signal is subjected to a peak hold processing to limit a signal detection range, thereby obtaining an envelope. The cycle of this envelope is obtained and the fine frequency difference is obtained. Furthermore, according to this value, the frequency of the object can be measured.

Figure 10A:
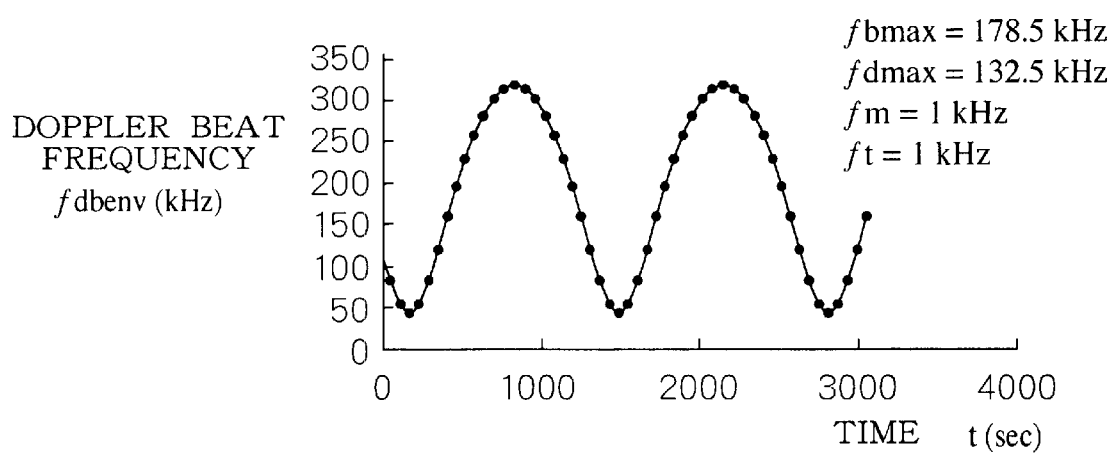
FIG. 10(A) shows an example when an object to be measured is driven by 1 kHz.
Figure 10B:
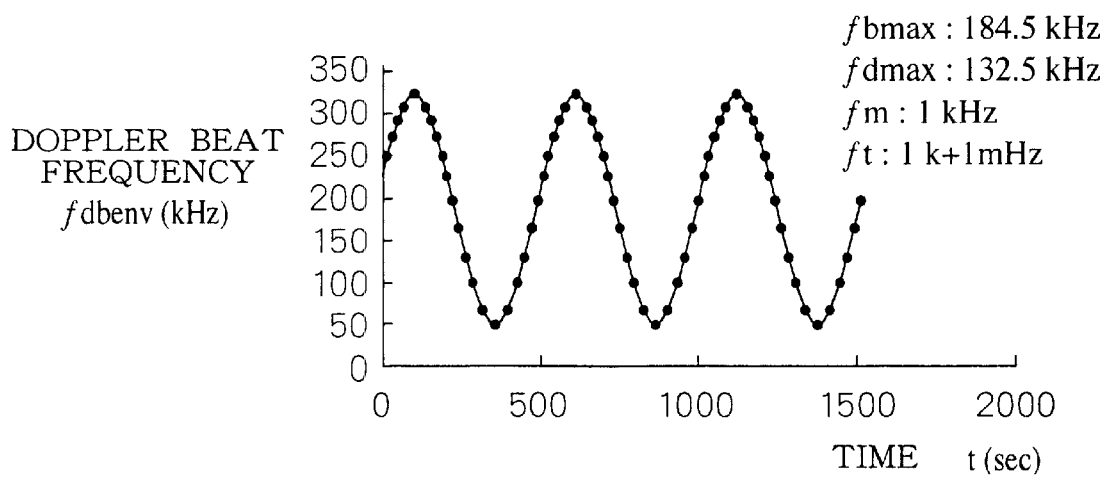
FIG. 10(B) shows an example when 1 mHz is increased.

FIG. 10(A) shows a transition of the envelope frequency $f_{dbenv}$ along the time when the modulation frequency $f_m$ and the object frequency $f_t$ are set to 1 kHz. The fine frequency difference $f_a$ calculated from this fluctuation cycle was found to be 0.725 mHz. Moreover, the object frequency $f_t$ was increased by 1 mHz and the same measurement was performed. As a result (FIG. 10 (B)), the fine frequency difference $f_a$ was calculated to be 1.923 mHz. Thus, increase of about 1 mHz was confirmed. This shows that for the set frequency 1 kHz, a relative frequency change in the order of $10^{-6}$ was measured. In order to obtain such an accuracy by using the conventional measurement method using a displacement meter, a sampling frequency of 1 GHz is required.

Moreover, when the laser modulation frequency is equal to the object frequency, this envelope shows a constant value and the processing to obtain an envelope is performed in the same way. When a fluctuation is observed, the laser modulation frequency is gradually changed and when the envelope has stopped its fluctuation, the laser modulation frequency is measured. This method enables to directly measure the object frequency.

Figure 11:
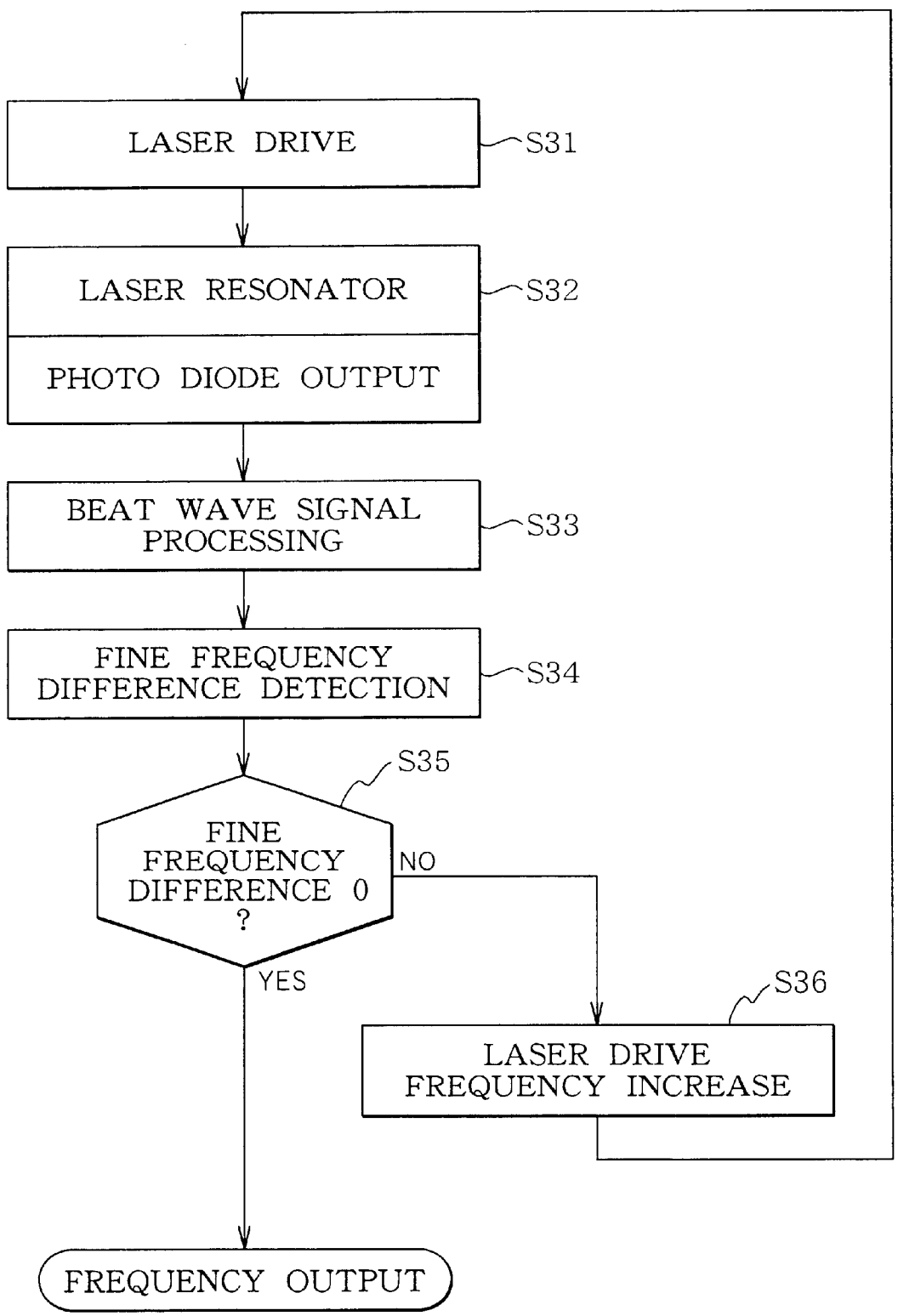
FIG. 11 is a flowchart showing a configuration of an example for determining a frequency of an object by synchronization.

FIG. 11 is a flowchart showing an example of the method for measuring an object oscillation cycle by changing the cycle of the sinusoidal wave drive current so as to be synchronized with the oscillation cycle of the object to be measured. In this example, the signal processor 21 has a synchronization control function for changing a drive current frequency in the laser drive block until the aforementioned envelope value reaches a constant value, and a frequency decision function for outputting as a frequency of the object a drive current frequency when the envelope value has reached a constant value by the synchronization control function.

In the example shown in FIG. 11, firstly, the laser is driven by a drive current having a frequency lower than an oscillation frequency of an object to be measured (step S31). Next, a return beam is self-mixed with an emitted beam in the laser resonator 14 and a resultant beat wave is output by the photo diode 20 (step S32). This beat wave is subjected to a signal processing (step S33) to detect a fine frequency difference (step S34). Then, it is determined whether the fine frequency difference is 0 (or not greater than a threshold value) (step S35). Unless the difference is 0, the laser drive frequency is increased (step S36). On the other hand, if the fine frequency difference is 0, the laser drive frequency is output as a frequency.

Next, an explanation will be given on a case when the fine frequency difference calculation function 22a in FIG. 2 calculates the frequency difference using the aforementioned envelope value change based on an approximation when a waveform of the envelope is assumed in advance. That is, explanation will be given on a method for reducing the time required for measurement.

$$f_{dmax}\sin 2\pi f_a(t_a + t) + f_{bmax} = f_{dbenv} \tag{5}$$

$$f_{dmax}\sin 2\pi f_a(t_a + t_1) + f_{bmax} = f_{dbenv1} \tag{6}$$

$$f_{dmax}\sin 2\pi f_a(t_a + t_1 + \Delta t) + f_{bmax} = f_{dbenv2} \tag{7}$$

$$f_a = \frac{1}{2\pi\Delta t}\left|\sin^{-1}\frac{f_{dbenv2} - f_{bmax}}{f_{dmax}} - \sin^{-1}\frac{f_{dbenv1} - f_{bmax}}{f_{dmax}}\right| \tag{8}$$

$$2f_{dmax}\left|\sin 2\pi\frac{f_a}{2}(t_a + t)\right| + f_{bmax} - f_{dmax} = f_{dbenv} \tag{9}$$

$$f_a = \frac{1}{2\pi\Delta t}\left|\cos^{-1}\left\{1 - \frac{(f_{dbenv2} - f_{bmax} + f_{dmax})^2}{2f_{dmax}^2}\right\} - \cos^{-1}\left\{1 - \frac{(f_{dbenv1} - f_{bmax} - f_{dmax})^2}{2f_{dmax}^2}\right\}\right| \tag{10}$$

Figures 12A, 12B:
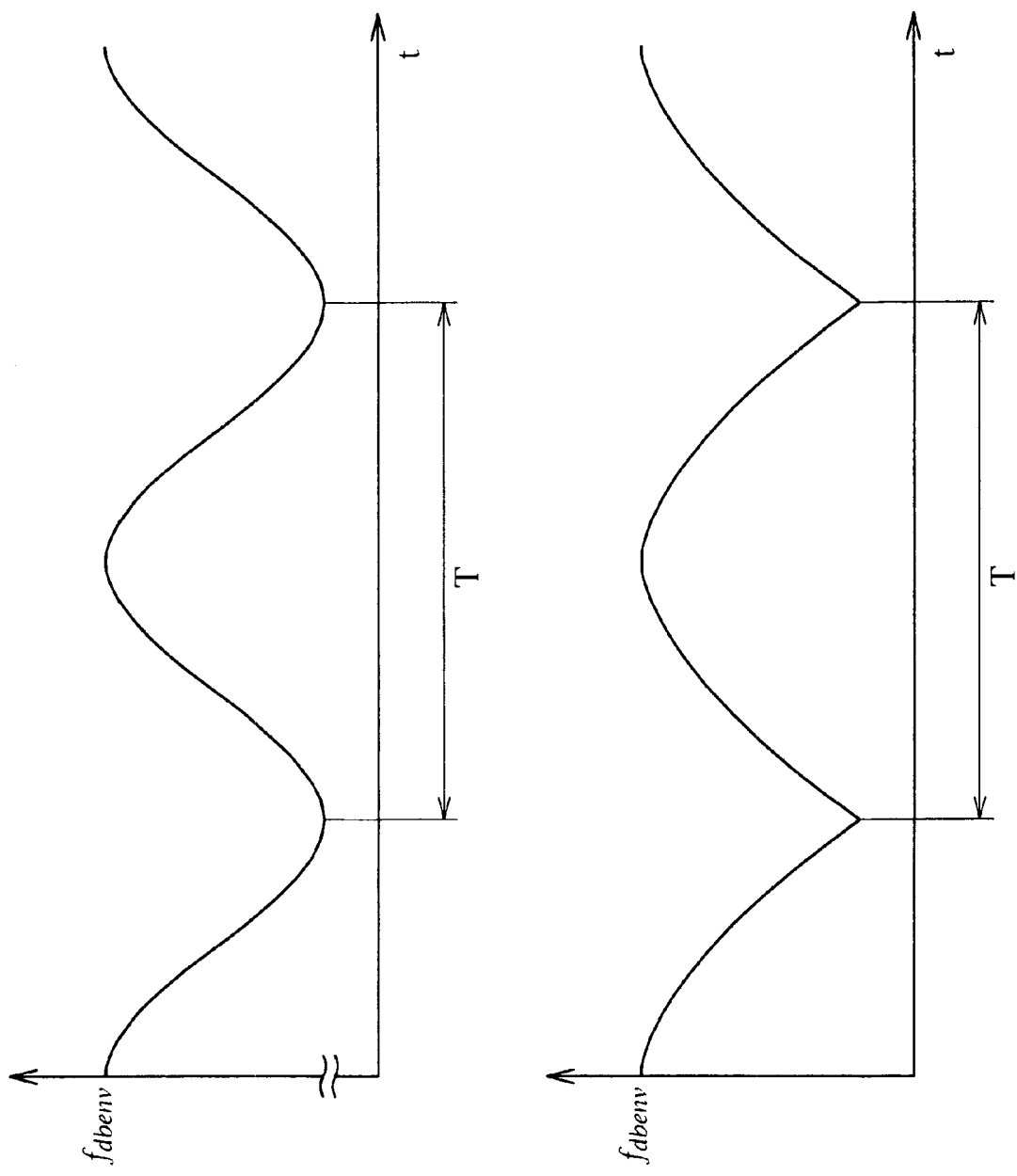
FIG. 12(A) shows a waveform example used in approximation 1.
FIG. 12(B) shows a waveform example used in approximation 2 and approximation 3.

In Equation (3), when the difference between $f_{bmax}$ and $f_{dmax}$ is small, the fluctuation of the envelope frequency $f_{dbenv}$ approaches the curve shown in FIG. 12(B), and as the difference increases, the fluctuation approaches the sinusoidal wave fluctuation shown in FIG. 12(A). Accordingly, it is possible to obtain a high accuracy by using Equation (8) when the difference between $f_{bmax}$ and $f_{dmax}$ is large, and Equation (10) when the difference is small.

It is possible to significantly reduce the measurement time by calculating the fine frequency difference $f_a$ between the semiconductor laser modulation frequency $f_m$ and the object frequency $f_t$ from a difference between measurement values at two points instead of the envelop cycle. The approximation may be a method assuming the envelope fluctuating in a sinusoidal wave as the first method or in an absolute value waveform as the second method.

[Approximation 1] If it is assumed that the envelope frequency $f_{dbenv}$ fluctuates in a sinusoidal wave, Equation (5) above is satisfied. Here, the time $t_a$ is a constant indicating a phase difference between $f_m$ and $f_t$. If it is assumed that the envelope frequency is $f_{dbenv1}$ at time $t_1$ and $f_{dbenv2}$ at time $t_1+\Delta t$, then Equation (5) can be expressed as Equation (6) and Equation (7). If the time $t_a+t_1$ is deleted from Equation (6) and (7) and then the Equations are transformed for the fine frequency difference $f_a$, then it is possible to obtain Equation (8) above.

[Approximation 2] When the envelope frequency $f_{dbenv}$ has the fluctuation shown in FIG. 12(B), Equation (9) is satisfied. Equation (9) can be transformed for the fine frequency difference $f_a$, and it is possible to obtain Equation (10) above. $f_a$ can be determined from this Equation (10).

[Approximation 3] If there is no difference between $f_{bmax}$ and $f_{dmax}$ in Equation (3), then Equation (10) has a high accuracy. For this, the laser frequency modulation efficiency df/di is recorded in advance and then the object oscillation is measured without modulating the laser, and the output $f_{dmax}$ from the photo diode 20 is recorded. The drive current amplitude is so that $f_{bmax}$ is equal to $f_{dmax}$ according to Equation (1).

Figure 13A:
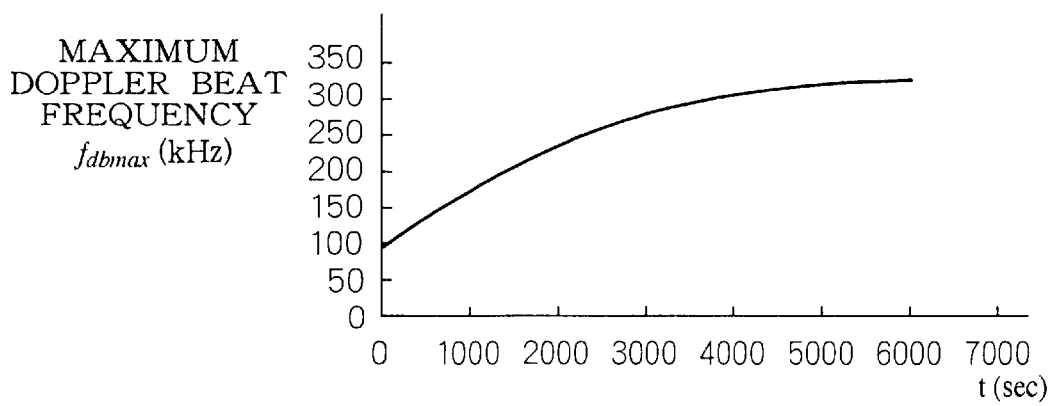
FIG. 13(A) shows characteristic of the maximum Doppler frequency along the time elapse.
Figure 13B:
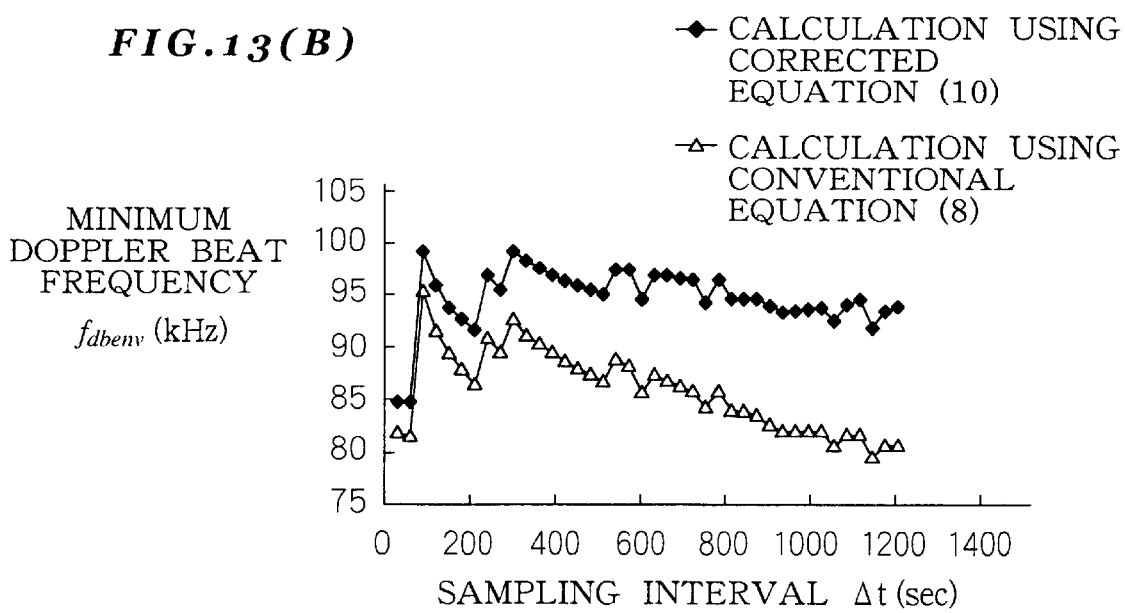
FIG. 13(B) is a waveform showing a calculation example of a small frequency difference with respect to a measurement time interval.

For the measurement result of the fine frequency difference shown in FIG. 13(A), Equation (8) and Equation (10) were used to obtain a fine frequency difference. The result is shown in FIG. 13(B). In this case, the difference between $f_{bmax}$ and $f_{dmax}$ is small and accordingly, the value calculated by Equation (10) has smaller error. As shown in FIG. 13(B), values obtained by Equation (10) show almost a constant value whereas values calculated by Equation (8) are gradually decreased showing no tendency for saturation.

According to the present invention having the aforementioned configuration, in the self-mixing step, a return beam from an object to be measured is self-mixed in the resonator with an emitted beam (oscillating beam) emitted upon return of this return beam so as to generate a beat wave in which the object Doppler frequency is superposed with the self-frequency, and the oscillation information output step outputs as the oscillation information of the object the beat wave obtained in the self-mixing step or information obtained from signal processing of this beat wave. Accordingly, an envelope (group frequency) based on a difference between the self-frequency based on the imaginary velocity of the resonator and the Doppler frequency based on the object velocity appears in the beat wave. When the resonator imaginary velocity is made constant, by detecting the change of this envelope, the object oscillation cycle change can be obtained. On the other hand, by successively changing the resonator imaginary velocity, it is possible to detect a frequency of the object. Furthermore, by calculating the envelope frequency or the envelope cycle, it is possible to calculate the object frequency with a high accuracy. Thus, the present invention provides various advantages over the prior art.

Moreover, in the frequency difference measuring apparatus according to the present invention, the laser drive block is driven by a laser drive current of a sinusoidal waveform and the laser resonator oscillates a wavelength changing according to the drive current, generating a self-frequency according to the resonator imaginary velocity which is the change velocity of this oscillated wavelength. On the other hand the return beam is added by the Doppler frequency according to the object velocity. When the emitted beam is self-mixed with the return beam in the resonator, a beat wave is generated as the result of superposing of the self-frequency with the Doppler frequency. The cycle change of this beat wave is a change based on a difference between the self-frequency and the Doppler frequency. Accordingly, by observing the frequency of this beat wave, it is possible to measure a frequency of the object and a frequency change. Thus, the present invention provides a frequency measuring apparatus having advantages over the prior art.

The invention may be embodied in other specific forms without departing from the spirit or essential characteristic thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

The entire disclosure of Japanese Patent Application No. 2000-36568 (Filed on Feb. 15, 2000) including specification, claims, drawings and summary are incorporated herein by reference in its entirety.

What is claimed is:

1. A frequency measuring apparatus comprising:
   a laser resonator that oscillates a laser beam to an object to be measured, and that self-mixes the laser beam reflected by the object, and returned as a return beam, with another laser beam emitted upon reception of the return beam;
   a laser drive that drives the laser resonator with a laser drive current having a sinusoidal wave;
   a laser that emits the laser beam, oscillated with a wavelength according to the laser drive current, in the laser resonator and that outputs a beat wave obtained from self-mixing the return beam with the emitted beam upon reception of the return beam; and
   a signal processor that processes the beat wave output from the laser and that outputs a processing result as an oscillation information,
   wherein the signal processor includes a frequency difference calculation function for calculating an oscillation frequency of the object according to a frequency change of the beat wave.

2. The frequency measuring apparatus as claimed in claim 1, wherein the signal processor includes an FV converter that converts the beat wave frequency into a voltage and a peak hold storage that holds a peak of the voltage value converted by the FV converter and outputs the peak value as an envelope waveform of the beat wave,
   wherein the frequency difference calculation function includes a function for calculating an oscillation frequency of the object to be measured, according to a cycle of the envelope waveform output from the peak hold storage.

3. The frequency measuring apparatus as claimed in claim 2, wherein the signal processor includes a synchronization control function that changes the drive current frequency in the laser drive until the envelope value reaches a constant value.

4. The frequency measuring apparatus as claimed in claim 1, wherein the frequency difference calculation function includes a function for calculating an oscillation frequency of the object using a change of the envelope value based on an approximation equation that assumes a waveform of the envelope.

5. The frequency measuring apparatus as claimed in claim 4, wherein the signal processor includes a synchronization control function that changes the drive current frequency in the laser drive until the envelope value reaches a constant value.

6. The frequency measuring apparatus as claimed in claim 1, wherein the signal processor includes a synchronization control function that changes the drive current frequency in the laser drive until an envelope value reaches a constant value.

7. An oscillation measuring method comprising:
   emitting a laser beam to an object to be measured;
   receiving a return beam reflected by the object and having an object Doppler frequency according to a velocity of the object;
   mixing the return beam having the Doppler frequency with another beam emitted upon reception of the return beam, and generating a self-frequency according to a resonator change during a time from the emission of the laser beam to the reception of the return beam, so as to generate a beat wave containing the object Doppler frequency superposed with the self-frequency; and outputting at least one of the beat wave and information obtained from signal processing of the beat wave as the object oscillation information.

8. The oscillation measuring method as claimed in claim 7, wherein the outputting includes: extracting an envelope of a frequency change waveform of the beat wave and calculating a frequency difference between the object Doppler frequency and the self-frequency according to a frequency of the extracted envelope.

9. A frequency measuring apparatus comprising:
- a laser resonator that oscillates a laser beam and self-mixes the oscillated beam reflected by a first object to be measured, and returned as a return beam, with another laser beam emitted upon reception of the return beam;
- a laser, arranged on a second object to be measured, that oscillates in synchronization with the oscillation of the first object, the laser holding the laser resonator; and
- a signal processor that processes a beat wave output from the laser block and that outputs a processing result as an oscillation information, wherein the signal processor includes a frequency difference calculation function for calculating a frequency difference between a frequency of the first object and a frequency of the second object according to an envelope of the beat wave.

* * * * *